United States Patent
Chao et al.

(10) Patent No.: US 10,791,947 B2
(45) Date of Patent: Oct. 6, 2020

(54) METHOD AND APPARATUS FOR UPDATING REFERENCE VERIFICATION INFORMATION USED FOR ELECTROCARDIOGRAM SIGNAL VERIFICATION

(71) Applicant: Samsung Electronics Co., Ltd., Suwon-si (KR)

(72) Inventors: Zhang Chao, Beijing (CN); Liu Yang, Beijing (CN); Chisung Bae, Yongin-si (KR); Sang Joon Kim, Hwaseong-si (KR); Liu Haixiao, Beijing (CN)

(73) Assignee: Samsung Electronics Co., Ltd., Suwon-si (KR)

( * ) Notice: Subject to any disclaimer, the term of this patent is extended or adjusted under 35 U.S.C. 154(b) by 261 days.

(21) Appl. No.: 15/868,665

(22) Filed: Jan. 11, 2018

(65) Prior Publication Data

US 2018/0192903 A1    Jul. 12, 2018

(30) Foreign Application Priority Data

Jan. 11, 2017 (CN) .......................... 2017 1 0017922
Sep. 26, 2017 (KR) ...................... 10-2017-0123951

(51) Int. Cl.
*A61B 5/04* (2006.01)
*A61B 5/0402* (2006.01)

(52) U.S. Cl.
CPC ........ *A61B 5/04012* (2013.01); *A61B 5/0402* (2013.01)

(58) Field of Classification Search
CPC .......................... A61B 5/04012; A61B 5/0402
See application file for complete search history.

(56) References Cited

U.S. PATENT DOCUMENTS

| 8,825,145 | B1 | 9/2014 | Zhang |
| 2015/0148696 | A1 | 5/2015 | Lall et al. |
| 2018/0330116 | A1* | 11/2018 | He ..................... A61B 5/04012 |

FOREIGN PATENT DOCUMENTS

| KR | 10-2016-0072682 A | 6/2016 |
| KR | 10-2016-0072705 A | 6/2016 |

* cited by examiner

*Primary Examiner* — Mallika D Fairchild
(74) *Attorney, Agent, or Firm* — NSIP Law

(57) ABSTRACT

A method to update reference verification information used for electrocardiogram (ECG) signal verification includes: identifying a first ECG signal measured from a user; verifying the first ECG signal by comparing a second ECG signal included in a reference ECG signal set with the first ECG signal; in response to the first ECG signal being successfully verified, setting the successfully verified first ECG signal to be a third ECG signal, and adding the third ECG signal to a verified ECG signal set; and updating the reference ECG signal set by setting the third ECG signal added to the verified ECG signal set to be an additional second ECG signal, based on the reference ECG signal set and the verified ECG signal set.

20 Claims, 9 Drawing Sheets

METHOD AND APPARATUS FOR UPDATING REFERENCE VERIFICATION INFORMATION USED FOR ELECTROCARDIOGRAM SIGNAL VERIFICATION

CROSS-REFERENCE TO RELATED APPLICATIONS

This application claims the benefit under 35 USC 119(a) of Chinese Patent Application No. 201710017922.7 filed on Jan. 11, 2017, in the State Intellectual Property Office of the P.R.C. and Korean Patent Application No. 10-2017-0123951 filed on Sep. 26, 2017, in the Korean Intellectual Property Office, the entire disclosures of which are incorporated herein by reference for all purposes.

BACKGROUND

1. Field

The following description relates to a method and apparatus for updating reference verification information used for electrocardiogram (ECG) signal verification.

2. Description of Related Art

Biometric authentication technology is used to perform user authentication using, for example, a fingerprint, an iris, a voice, a face, or an electrocardiogram (ECG) signal. Such biological characteristics used for the authentication differ from individual to individual, rarely change during a lifetime, and have a low risk of being stolen or copied. In addition, individuals do not need to intentionally carry such characteristics at all times, and thus may not experience inconvenience using the biological characteristics. An ECG signal-based authentication method, which is a type of the biometric authentication technology, may be effective in that an ECG signal is not readily copied or forged, and is relatively highly stable and identifiable. Thus, such an ECG signal-based authentication method has recently been attracting a growing interest.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method to update reference verification information used for electrocardiogram (ECG) signal verification includes: identifying a first ECG signal measured from a user; verifying the first ECG signal by comparing a second ECG signal included in a reference ECG signal set with the first ECG signal; in response to the first ECG signal being successfully verified, setting the successfully verified first ECG signal to be a third ECG signal, and adding the third ECG signal to a verified ECG signal set; and updating the reference ECG signal set by setting the third ECG signal added to the verified ECG signal set to be an additional second ECG signal, based on the reference ECG signal set and the verified ECG signal set.

The second ECG signal may be among second ECG signals included in the reference ECG signal set. The verifying of the first ECG signal may include determining a verification threshold value based either one or both of a similarity between second ECG signals included in the reference ECG signal set and a number of the second ECG signals, determining a similarity between the first ECG signal and the second ECG signal, and verifying the first ECG signal by comparing the determined verification threshold value with the determined similarity.

The third ECG signal added to the verified ECG signal set may be among third ECG signals included in the verified ECG signal set. The updating of the reference ECG signal set may include setting the third ECG signal added to the verified ECG signal set to be the additional second ECG signal and adding the additional second ECG signal to the reference ECG signal set, in response to a number of the third ECG signals included in the verified ECG signal set being greater than or equal to a update threshold value.

The second ECG signal may be among second ECG signals included in the reference ECG signal set, and the third ECG signal added to the verified ECG signal set may be among third ECG signals included in the verified ECG signal set. The updating of the reference ECG signal set may further include determining a similarity between each of the second ECG signals included in the reference ECG signal set and each of the third ECG signals included in the verified ECG signal set, classifying the third ECG signals into groups based on the determined similarity, setting the third ECG signal added to the verified ECG signal set to be the additional second ECG signal, in response to the third ECG signal added to the verified ECG signal set being included in a group including one or more of the second ECG signals based on a result of the classifying, and adding the additional second ECG signal to the reference ECG signal set.

The classifying of the third ECG signals into groups may include classifying, into a first group, a third ECG signal, among the third ECG signals, having a similarity with a second ECG signal, among the second ECG signals, that is greater than or equal to a first grouping threshold value, classifying, into a second group, a third ECG signal, among the third ECG signals, having a similarity with a second ECG signal, among the second ECG signals, that is less than the first grouping threshold value and having a similarity with another third ECG signal, among the third ECG signals, that is greater than or equal to a second grouping threshold value, and classifying, into a third group, a third ECG signal, among the third ECG signals, that is not included in either one of the first group and the second group.

The adding of the second ECG signal to the reference ECG signal set may include setting the third ECG signal classified into the first group and the third ECG signal classified into the second group to be additional second ECG signals, and adding the additional second ECG signals to the reference ECG signal set.

The second ECG signal may be among second ECG signals included in the reference ECG signal set, and the third ECG signal added to the verified ECG signal set may be among third ECG signals included in the verified ECG signal set. The updating of the reference ECG signal set may include determining a similarity between each of the second ECG signals included in the reference ECG signal set and each of the third ECG signals included in the verified ECG signal set generating an undirected graph associated with the second ECG signals and the third ECG signals based on the determined similarity, classifying the second ECG signals and the third ECG signals into two groups by applying, to the generated undirected graph, a minimum cut based on the determined similarity, setting the third ECG signal added to the verified ECG signal set to be the additional second ECG signal, in response to the third ECG signal added to the verified ECG signal set being in a group, among the two groups, including the second ECG signal, and adding the additional second ECG signal to the reference ECG signal set.

The generating of the undirected graph may include connecting each of the second ECG signals and each of the third ECG signals through a connection line with the determined similarity set as a weight.

The generating of the undirected graph may further include simplifying the undirected graph by removing a connection line with a weight less than or equal to a simplification threshold value.

The second ECG signal may be among second ECG signals included in the reference ECG signal set. The updating of the reference ECG signal set may include determining a sum of similarities with the second ECG signals for each of the second ECG signals and removing a second ECG signal with a maximum sum of similarities, in response to a number of the second ECG signals included in the reference ECG signal set being greater than or equal to a removal threshold value.

In another general aspect, a non-transitory computer-readable storage medium may store instructions that, when executed by a processor, cause a processor to perform the method described above.

In another general aspect, an electrocardiogram (ECG) signal verification apparatus to update reference verification information used for ECG signal verification includes: a processor; and a memory configured to store one or more instructions implementable by the processor. In response to the one or more instructions being implemented by the processor, the processor is configured to identify a first ECG signal measured from a user for ECG signal verification for the user, verify the first ECG signal using a reference ECG signal set including a second ECG signal to be compared with the first ECG signal, in response to the first ECG signal being successfully verified, set the successfully verified first ECG signal to be a third ECG signal and add the third ECG signal to a verified ECG signal set, and update the reference ECG signal set by setting the third ECG signal added to the verified ECG signal set to be an additional second ECG signal.

The second ECG signal may be among second ECG signals included in the reference ECG signal set. The processor may be further configured to determine a verification threshold value based on either one or both of a similarity between second ECG signals included in the reference ECG signal set and a number of the second ECG signals, determine a similarity between the first ECG signal and the second ECG signal included in the reference ECG signal set, and verify the first ECG signal by comparing the determined verification threshold value with the determined similarity between the first ECG signal and the second ECG signal.

The second ECG signal may be among second ECG signals included in the reference ECG signal set, and the third ECG signal added to the verified ECG signal set may be among third ECG signals included in the verified ECG signal set. The processor may be further configured to determine a similarity between each of second ECG signals included in the reference ECG signal set and each of third ECG signals included in the verified ECG signal set, classify the third ECG signals into groups based on the determined similarity, set the third ECG signal added to the verified ECG signal set to be the additional second ECG signal, in response to the third ECG signal added to the verified ECG signal set being included in a group including one or more of the second ECG signals based on a result of the classifying, and add the additional second ECG signal to the reference ECG signal set.

The processor may be further configured to: classify, into a first group, a third ECG, among the third ECG signals, signal having a similarity with a second ECG signal, among the second ECG signals, that is greater than or equal to a first grouping threshold value, classify, into a second group, a third ECG signal, among the third ECG signals, having a similarity with a second ECG signal, among the second ECG signals, that is less than the first grouping threshold value and having a similarity with another third ECG signal, among the third ECG signals, that is greater than or equal to a second grouping threshold value, and classify, into a third group, a third ECG, among the third ECG signals, that is not included in either one of the first group and the second group.

The processor may be further configured to set the third ECG signal included in the first group and the third ECG signal included in the second group to be additional second ECG signals, and add the additional second ECG signals to the reference ECG signal set.

The second ECG signal may be among second ECG signals included in the reference ECG signal set, and the third ECG signal added to the verified ECG signal set may be among third ECG signals included in the verified ECG signal set. The processor may be further configured to determine a similarity between each of the second ECG signals included in the reference ECG signal set and each of the third ECG signals included in the verified ECG signal set, generate an undirected graph associated with the second ECG signals and the third ECG signals based on the determined similarity, classify, into two groups, the second ECG signals and the third ECG signals by applying, to the generated undirected graph, a minimum cut based on the determined similarity, set the third ECG signal added to the verified ECG signal set to be the additional second ECG signal, in response to the third ECG signal added to the verified ECG signal set being in a group, among the two groups, including the second ECG, and add the additional second ECG signal to the reference ECG signal set.

The processor may be further configured to connect each of the second ECG signals and each of the third ECG signals through a connection line with the determined similarity set as a weight.

The processor may be further configured to simplify the undirected graph by removing a connection line with a weight less than or equal to a simplification threshold value.

The second ECG signal may be among second ECG signals included in the reference ECG signal set. The processor may be further configured to determine a sum of similarities with the second ECG signals for each of the second ECG signals and remove a second ECG signal, among the second ECG signals, with a maximum sum of similarities, in response to a number of the second ECG signals included in the reference ECG signal set being greater than or equal to a removal threshold value.

Other features and aspects will be apparent from the following detailed description, the drawings, and the claims.

Figure 1:
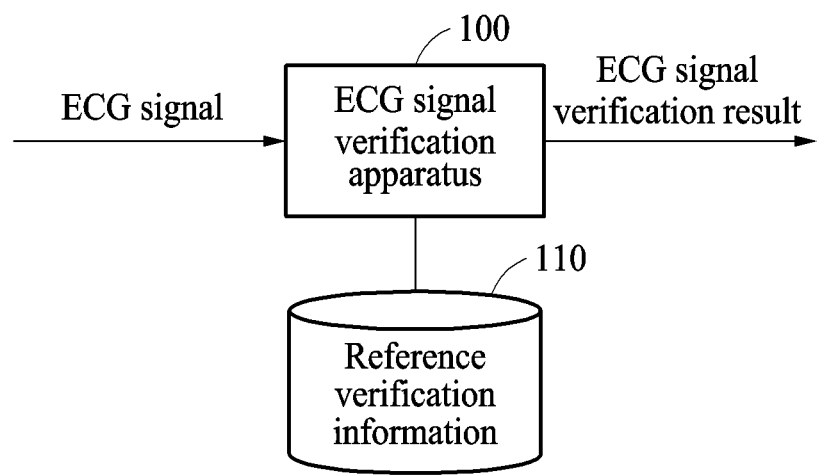
FIG. 1 is a diagram illustrating an example of a method of updating reference verification information.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after gaining a thorough understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Terms such as first, second, A, B, (a), (b), and the like may be used herein to describe components. Each of these terminologies is not used to define an essence, order, or sequence of a corresponding component but used merely to distinguish the corresponding component from other component(s). For example, a first component may be referred to as a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing.

The terminology used herein is for the purpose of describing particular embodiments only and is not intended to be limiting. For example, as used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, operations, elements, components or one or more combinations/groups thereof in one or more example embodiments, but do not preclude the presence or addition of one or more other features, integers, operations, elements, components, and/or combinations/groups thereof in alternative embodiments, nor the lack of such stated features, integers, operations, elements, and/or components, and/or combinations/groups in further alternative embodiments unless the context and understanding of the present disclosure indicates otherwise. In addition, the use of the term "may" herein with respect to an example or embodiment, e.g., as to what an example or embodiment may include or implement, means that at least one example or embodiment exists where such a feature is included or implemented while all examples and embodiments are not limited thereto.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Also, in the description of embodiments, detailed description of well-known related structures or functions will be omitted when it is deemed that such description will cause ambiguous interpretation of the present disclosure.

Examples to be described hereinafter are applicable to recognize an electrocardiogram (ECG) signal of a user. The recognizing of an ECG signal of a user may include authenticating or identifying the user. The authenticating of the user may include determining whether the user is a preregistered user. A result of the authenticating may be output as true or false. The identifying of the user may include determining a preregistered user, among preregistered users, to which the user corresponds. A result of the identifying of the user may be output as an identification (ID) of the one of the preregistered users. In response to the user not corresponding to any one of the preregistered users, the result of the identifying of the user may be output as a signal indicating that the user is not identified.

Examples to be described hereinafter may be embodied in various forms of products, for example, a personal computer (PC), a laptop computer, a tablet PC, a smartphone, a television (TV), a smart home appliance, an intelligent vehicle, a kiosk, and a wearable device. The examples are applicable to user authentication used in, for example, a smartphone, a mobile device, and a smart home system. In addition, the examples may be applicable to a payment service based on the user authentication. Further, the examples may also be applicable to a smart vehicle system that is automatically started through the user authentication. Hereinafter, example embodiments are described in detail with reference to the accompanying drawings in which like reference numerals indicate like elements.

FIG. 1 is a diagram illustrating an example of a method of updating reference verification information.

FIG. 1 illustrates an electrocardiogram (ECG) signal verification apparatus 100 and reference verification information 110. The ECG signal verification apparatus 100 is, for example, an apparatus configured to perform ECG signal verification by verifying an ECG signal input to the ECG signal verification apparatus 100 and outputting a result of the verifying. The ECG signal input to the ECG signal verification apparatus 100 will be hereinafter referred to as a "first ECG signal" to distinguish it from other ECG signals described herein.

The ECG signal verification apparatus 100 may be embedded or incorporated in various types of devices, for example, a mobile phone, a cellular phone, a smartphone, a PC, a laptop, a notebook, a subnotebook, a netbook, a tablet computer (tablet), a phablet, a personal digital assistant (PDA), a digital camera, a portable game console, an MP3 player, a portable/personal multimedia player (PMP), a handheld e-book, a global positioning system (GPS) navigation, a personal/portable navigation device (PND), a handheld game console, a disk player, a set-top box, a home appliance, a communication device, a display device, and other electronic devices, or may interwork with the example devices described above. In addition, the ECG signal verification apparatus 100 may also be embedded or incorporated in a smart home appliance, an intelligent vehicle, an autonomous driving vehicle, a smart home environment, a smart building environment, a smart office environment, a smart electronic security system, and other devices, environments, and systems, or may interwork with the example devices, environments, and systems described above. Further, the ECG signal verification apparatus 100 may be included in a wearable device that is worn on or around a body of a user to operate or interwork with the wearable device. The wearable device includes, for example, a ring, a watch, a pair of glasses, a bracelet, an ankle bracket, a belt, a necklace, an earring, a headband, a helmet, and a device embedded in cloth.

The reference verification information 110 is, for example, information to be used for the ECG signal verification apparatus 100 to refer to when verifying a first ECG signal. The reference verification information 110 may include an ECG signal initially registered by a user or ECG signals that are updated through verification performed multiple times. The ECG signal verification apparatus 100 may verify the first ECG signal by comparing the first ECG signal, which is an input ECG signal, to the reference verification information 110.

The reference verification information 110 may include a reference ECG signal set, which is a set of reference ECG signals. A reference ECG signal is an ECG signal with which the ECG signal verification apparatus 100 compares the first ECG signal for ECG signal verification for a user. The reference ECG signal may include an ECG signal that is initially registered by the user. The reference ECG signal will be hereinafter referred to as a "second ECG signal" to distinguish it from other ECG signals described herein.

The ECG signal verification apparatus 100 stores, in the reference ECG signal set, a second ECG signal in a suitable form such as a feature vector or a key point extracted from the second ECG signal. For example, the ECG signal verification apparatus 100 processes an ECG signal measured from the user and extracts a feature vector from the processed ECG signal to be used as a second ECG signal.

The ECG signal verification apparatus 100 processes the ECG signal through, for example, filtering, key point extraction, and segmentation. The ECG signal verification apparatus 100 also extracts the feature vector using, for example, a trained neural network.

The ECG signal verification apparatus 100 identifies the first ECG signal measured from the user. For example, the ECG signal verification apparatus 100 identifies the first ECG signal through an embedded sensor or other devices. The ECG signal verification apparatus 100 may identify the first ECG signal measured from the user through other suitable methods.

The ECG signal verification apparatus 100 may identify the first ECG signal measured from the user in response to an operation or function needed for the ECG signal verification. The operation or function needed for the ECG signal verification includes, for example, canceling a screen lock, making a payment, or opening an encoded file.

The ECG signal verification apparatus 100 may then verify the first ECG signal by comparing the first ECG signal with a second ECG signal included in the reference ECG signal set. For example, the ECG signal verification apparatus 100 determines a similarity between the first ECG signal and the second ECG signal, and determines whether to verify the first ECG signal. The ECG signal verification apparatus 100 determines whether the first ECG signal is measured from a same user based on the similarity between the first ECG signal and the second ECG signal.

The ECG signal verification may be more effective in comparison to facial recognition, fingerprint recognition, and voice or speech recognition, because the ECG signal verification is relatively more robust against a fake or forgery. However, although ECG signals are obtained from a same user, the ECG signals may be different from one another based on a state or condition of the user. For example, an ECG signal may vary greatly before and after exercise, before and after a meal, or before and after a change of mood.

For the ECG signal verification for the user being in a certain state, the user registers a second ECG signal in the ECG signal verification apparatus 100. The ECG signal verification apparatus 100 then verifies first ECG signals that are input by the user and correspond to various states of the user through the ECG signal verification being performed multiple times. The ECG signal verification apparatus 100 then updates the reference verification information 110 using successfully verified first ECG signals.

The ECG signal verification apparatus 100 sets a successfully verified first ECG signal to be a third ECG signal, and adds the third ECG signal to a verified ECG signal set. A third ECG signal as used herein is an ECG signal that is successfully verified in the ECG signal verification, and the verified ECG signal set is a set of such third ECG signals. The verified ECG signal set is used to update the reference verification information 110.

The ECG signal verification apparatus 100 updates the reference ECG signal set using ECG signals included in the reference ECG signal set and the verified ECG signal set. The ECG signal verification apparatus 100 filters a third ECG signal out of the verified ECG signal set and sets the filtered third ECG signal to be an additional second ECG signal. The ECG signal verification apparatus 100 then adds the additional second ECG signal to the reference ECG signal set. The ECG signal verification apparatus 100 also removes a portion (e.g., one or more) of second ECG signals included in the reference ECG signal set.

The ECG signal verification apparatus 100 updates the reference ECG signal set by accumulating, in the reference ECG signal set, an ECG signal included in one of the reference ECG signal set and the verified ECG signal set. Thus, accuracy in the ECG signal verification performed by the ECG signal verification apparatus 100 is improved. In addition, the ECG signal verification apparatus 100 verifies first ECG signals that are identified in various states or conditions of the user.

Figure 2A:
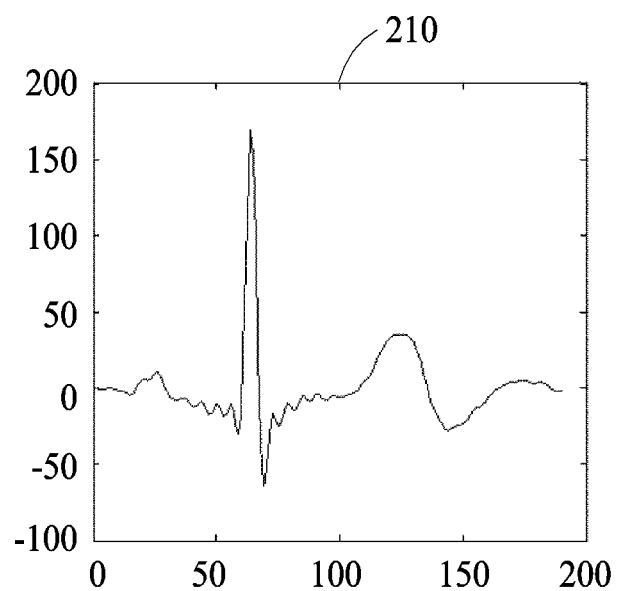
FIGS. 2A and 2B are diagrams illustrating an example of a first electrocardiogram (ECG) signal and an example of a second ECG signal, respectively.
Figure 2B:
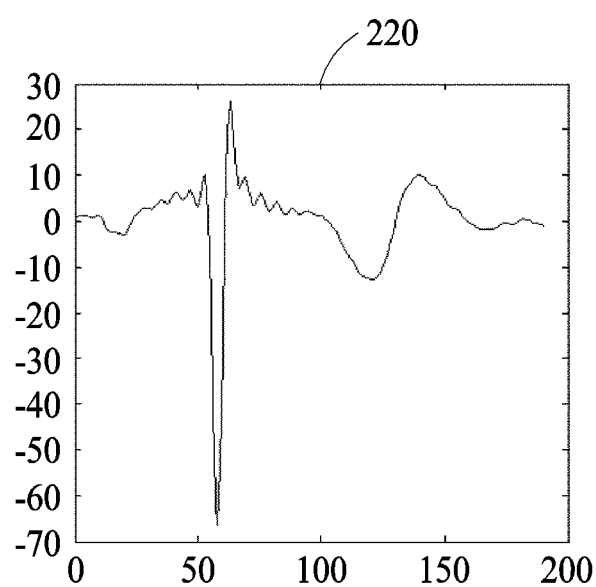

FIGS. 2A and 2B are diagrams illustrating an example of a first ECG signal and an example of a second ECG signal.

FIG. 2A illustrates a first ECG signal 210, and FIG. 2B illustrates a second ECG signal 220. Referring to FIGS. 2A and 2B, the ECG signal verification apparatus 100 identifies the first ECG signal 210 measured from a user for ECG signal verification for the user. The ECG signal verification apparatus 100 then verifies the first ECG signal 210 using a reference ECG signal set including the second ECG signal 220. In a case in which the user registers the second ECG signal 220 and initially attempts at the ECG signal verification, the reference ECG signal set may include only the second ECG signal 220.

As illustrated, although the ECG signals 210 and 220 are identified from the same user, the first ECG signal 210 and the second ECG signal 220 are significantly different from each other. For example, the user may register the second ECG signal 220 before exercise. The ECG signal verification apparatus 100 may then identify the first ECG signal 210 from the user after the exercise. In such an example, the ECG signal verification apparatus 100 may determine that the first ECG signal 210 and the second ECG signal 220 are from different users.

The ECG signal verification apparatus 100 updates the reference ECG signal set through performing the ECG signal verification multiple times. The reference ECG signal set may then include additional second ECG signals in addition to the second ECG signal 220. The ECG signal verification apparatus 100 verifies the first ECG signal 210 by comparing the first ECG signal 210 and a second ECG signal included in the reference ECG signal set.

In an example, the ECG signal verification apparatus 100 determines a similarity between the first ECG signal 210 and the second ECG signal. In response to the determined similarity being greater than or equal to a verification threshold value, the ECG signal verification apparatus 100 determines that the first ECG signal 210 is successfully verified. The verification threshold value used herein is a similarity threshold to be used for the first ECG signal 210 to be successfully verified. The verification threshold value may be a preset value, or a value determined by the ECG signal verification apparatus 100 based on the reference ECG signal set.

Hereinafter, an example of a manner in which the ECG signal verification apparatus 100 updates reference verification information to be used for ECG signal verification will be described in greater detail.

Figure 3:
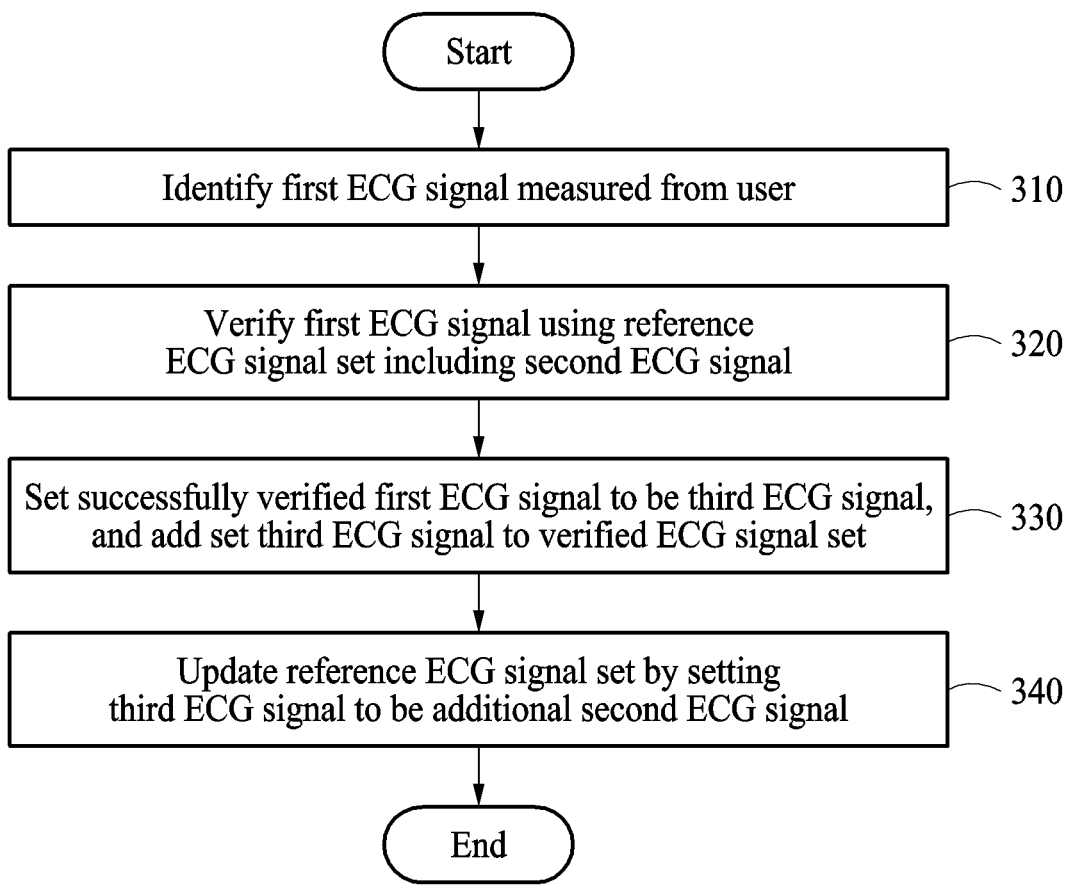
FIG. 3 is a flowchart illustrating an example of a method of updating reference verification information.

FIG. 3 is a flowchart illustrating an example of a method of updating reference verification information.

The method of updating reference verification information to be described hereinafter may be performed by the ECG signal verification apparatus 100. In addition, although not illustrated, the method of updating reference verification information may be implemented by a processor included in the ECG signal verification apparatus 100. The processor used herein may be embodied by a software module, a hardware module, or combinations thereof.

Referring to FIG. 3, in operation 310, the ECG signal verification apparatus 100 identifies a first ECG signal measured from a user for ECG signal verification for the user. For example, the ECG signal verification apparatus 100 identifies the first ECG signal from the user through an embedded sensor or other devices.

In operation 320, the ECG signal verification apparatus 100 verifies the first ECG signal using a reference ECG signal set including a second ECG signal to be compared with the first ECG signal. The ECG signal verification apparatus 100 provides the user with a result of the verifying, which indicates whether the first ECG signal is successfully verified.

The reference ECG signal set includes one or more second ECG signals. For example, the reference ECG signal set includes a second ECG signal that is initially registered by the user. The ECG signal verification apparatus 100 may add or remove a second ECG signal to or from the reference ECG signal set through updating.

In an example, the ECG signal verification apparatus 100 determines a similarity between the first ECG signal and each of second ECG signals included in the reference ECG signal set. The ECG signal verification apparatus 100 extracts a feature vector of the first ECG signal, and determines a similarity between the extracted feature vector and a feature vector of each of the second ECG signals. The ECG signal verification apparatus 100 compares the determined similarity with a verification threshold value to determine whether the first ECG signal is successfully verified. The ECG signal verification apparatus 100 compares, to the verification threshold value, a sum of the determined similarities, an average value of the determined similarities, or a maximum value or a minimum value among the determined similarities to verify the first ECG signal. In response to the maximum value of the similarities being greater than the verification threshold value, the ECG signal verification apparatus 100 determines that the first ECG signal is successfully verified.

The ECG signal verification apparatus 100 may determine the similarity between the first ECG signal and each of the second ECG signals using various methods. The ECG signal verification apparatus 100 determines the similarity between the first ECG signal and each of the second ECG signals using, for example, a cosine distance, a cosine similarity, a Pearson correlation coefficient, a Euclid distance, a Minkowski distance, or a Mahalanobis distance.

The ECG signal verification apparatus 100 calculates the verification threshold value based on the reference ECG signal set. For example, the ECG signal verification apparatus 100 determines the verification threshold value based on any one or any combination of any two or more of the number of the second ECG signals included in the reference ECG signal set, a minimum value of similarities among the second ECG signals, and a maximum value of the similarities among the second ECG signals. In addition, the ECG signal verification apparatus 100 calculates again the verification threshold value each time the ECG signal verification apparatus 100 updates the reference ECG signal set.

For example, the ECG signal verification apparatus 100 calculates the verification threshold value using the following Equation 1.

$$Thre = p \cdot F \qquad \text{[Equation 1]}$$

In Equation 1, Thre is a verification threshold value. F is a vector indicating a state of a reference ECG signal set. F is any one or any combination of any two or more of the number of second ECG signals included in the reference ECG signal set, a minimum value of similarities among the second ECG signals, an average value of the similarities among the second ECG signals, and a maximum value of the similarities among the second ECG signals.

p is an empirical coefficient. p may be obtained using a pair of different pieces of training data. Each pair of training data may include a verification threshold value corresponding to a preset value of a false rejection rate based on F and the reference ECG signal set. The false rejection rate indicates a probability that a first ECG signal of the same user fails to be verified. For example, each pair of training data includes a verification threshold value corresponding to F and the false rejection rate being 5%. The ECG signal verification apparatus 100 may obtain p using a linear regression method.

The ECG signal verification apparatus 100 calculates the similarity between the first ECG signal and each of the second ECG signals included in the reference ECG signal set. The ECG signal verification apparatus 100 compares the calculated similarity and the verification threshold value, and determines whether the first ECG signal is successfully verified. For example, a second ECG signal measured when the user is at a standstill is included in the reference ECG signal set. In such an example, the ECG signal verification apparatus 100 calculates the verification threshold value using the second ECG signal measured from the user being at a standstill, without a need to calculate the verification threshold value when the user is in motion or in a dynamic state. The verification threshold value may also be a preset value.

In operation 330, in response to the first ECG signal being successfully verified, the ECG signal verification apparatus 100 sets the successfully verified first ECG signal to be a third ECG signal, and adds the third ECG signal to a verified ECG signal set. The ECG signal verification apparatus 100 adds, in a form of a feature vector, the successfully verified first ECG signal to the verified ECG signal set. When the ECG signal verification is performed multiple times, the number of third ECG signals to be added to the verified ECG signal set may increase.

In operation 340, the ECG signal verification apparatus 100 updates the reference ECG signal set by setting the third ECG signal included in the verified ECG signal set to be an additional second ECG signal based on the reference ECG signal set and the verified ECG signal set.

When a preset condition is satisfied, the ECG signal verification apparatus 100 updates the reference ECG signal set. In an example, in response to the number of third ECG signals included in the verified ECG signal set being greater than or equal to an update threshold value, the ECG signal verification apparatus 100 updates the reference ECG signal set. The update threshold value used herein refers to a minimum value of the number of third ECG signals to update the reference ECG signal set. When a third ECG signal is accumulated in the verified ECG signal set, the ECG signal verification apparatus 100 updates the reference ECG signal set.

The ECG signal verification apparatus 100 sets, to be an additional second ECG signal, a portion (e.g., one or more) of the third ECG signals included in the verified ECG signal set or all of the third ECG signals included in the verified ECG signal set. In addition, the ECG signal verification apparatus 100 may not set, to be an additional second ECG signal, a third ECG signal included in the verified ECG signal set. The ECG signal verification apparatus 100 determines whether to set a third ECG signal to be an additional second ECG signal using a similarity of each of signals included in the reference ECG signal set and the verified ECG signal set.

The ECG signal verification apparatus 100 adds the newly set, additional second ECG signal to the reference ECG signal set. In addition, the ECG signal verification apparatus 100 removes a portion (e.g., one or more) of the second ECG signals included in the reference ECG signal set. Further, the ECG signal verification apparatus 100 updates the verification threshold value based on the updated reference ECG signal set.

In an example, the ECG signal verification apparatus 100 classifies, into groups, the second ECG signals and the third ECG signals based on the similarity of each of the signals included in the reference ECG signal set and the verified ECG signal set. The ECG signal verification apparatus 100 then sets a third ECG signal included in a group including a second ECG signal to be an additional second ECG signal based on a result of the classifying, and adds the additional second ECG signal to the reference ECG signal set.

In another example, the ECG signal verification apparatus 100 determines the similarity of each of the signals included in the reference ECG signal set and the verified ECG signal set. The ECG signal verification apparatus 100 then generates an undirected graph associated with the second ECG signals and the third ECG signals using the determined similarity. The ECG signal verification apparatus 100 applies a minimum cut to the generated undirected graph based on the determined similarity. The ECG signal verification apparatus 100 sets, to be an additional second ECG signal, a third ECG signal connected to a second ECG signal after applying the minimum cut to the undirected graph, and adds the additional second ECG signal to the reference ECG signal set.

Examples of a method of updating a reference ECG signal set by the ECG signal verification apparatus 100 will be described in greater detail with reference to FIGS. 4 through 8.

Figure 4:
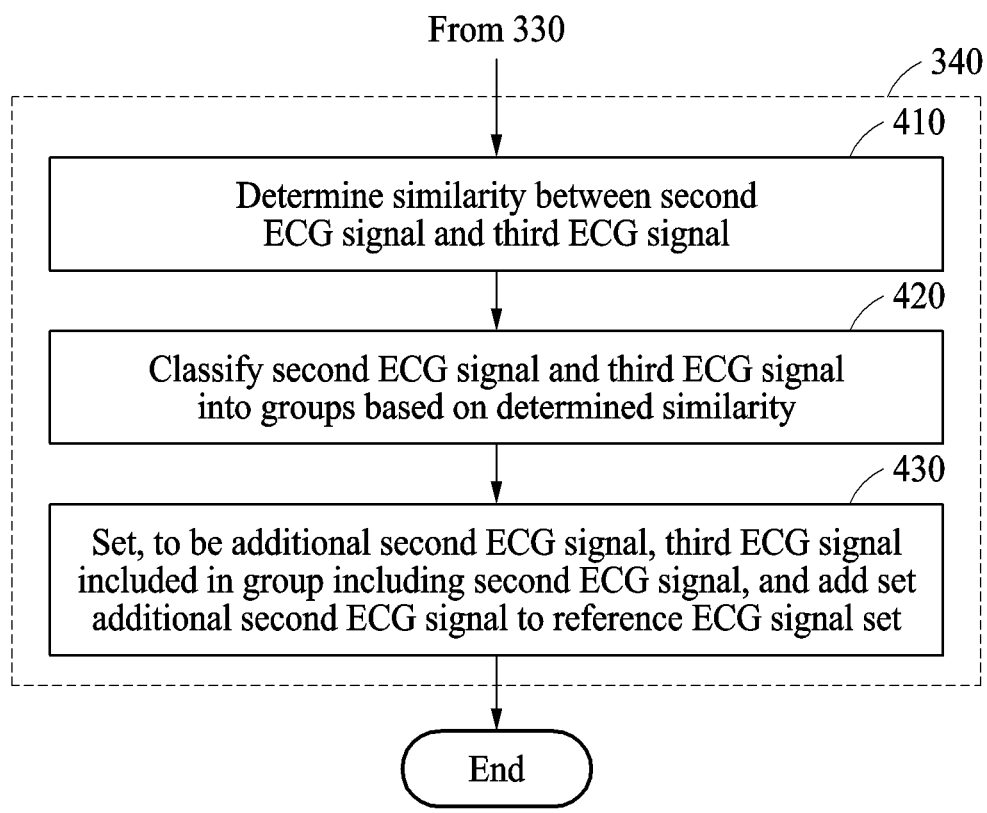
FIG. 4 is a flowchart illustrating an example of a method of updating a reference ECG signal set.

FIG. 4 is a flowchart illustrating an example of a method of updating a reference ECG signal set.

Operation 340 described above with reference to FIG. 3 may include operations 410 through 430 to be described hereinafter with reference to FIG. 4. Referring to FIG. 4, in operation 410, the ECG signal verification apparatus 100 determines a similarity between each of second ECG signals included in a reference ECG signal set and each of third ECG signals included in a verified ECG signal set. For example, for a single second ECG signal, the ECG signal verification apparatus 100 determines a similarity with each of remaining second ECG signals among the second ECG signals, and a similarity with each of the third ECG signals. Similarly, for a single third ECG signal, the ECG signal verification apparatus 100 determines a similarity with each of remaining third ECG signals among the third ECG signals, and a similarity with each of the second ECG signals.

In operation 420, the ECG signal verification apparatus 100 classifies the third ECG signals into groups based on the determined similarity. The ECG signal verification apparatus 100 classifies the second ECG signals and the third ECG signals into a single group or a plurality of groups.

The ECG signal verification apparatus 100 classifies, into a first group, a third ECG signal having a similarity with a second ECG signal that is greater than or equal to a first grouping threshold value. The first group is a group including a second ECG signal and a third ECG signal having a relatively high similarity with the second ECG signal. The first grouping threshold value is a reference value used to determine a third ECG signal to be included in the first group. The first grouping threshold value may be a preset value. Alternatively, the ECG signal verification apparatus 100 may set the first grouping threshold value based on the determined similarity. For example, the first grouping threshold value is determined using a similarity of each of a certain portion (e.g., number) of the third ECG signals, among the third ECG signals included in the verified ECG signal set, that has a relatively high similarity with a second ECG signal. A third ECG signal and a second ECG signal included in the first group may be ECG signals that are measured in similar states of a user.

The ECG signal verification apparatus 100 classifies, into a second group, a third ECG signal having a similarity with a second ECG signal that is less than the first grouping threshold value and a similarity with another third ECG signal that is greater than or equal to a second grouping threshold value. The second group is a group of third ECG signals having a similarity with a second ECG signal that is less than the first grouping threshold value and a similarity with another third ECG signal that is greater than or equal to the second grouping threshold value. The second grouping threshold value is a reference value used to determine a third ECG signal to be included in the second group. The second grouping threshold value may be a preset value. Alternatively, the ECG signal verification apparatus 100 may determine the second grouping threshold value based on the determined similarity. For example, the second grouping threshold value may be determined based on a similarity between the third ECG signals. The third ECG signal included in the second group may be an ECG signal measured in a state that is different from a state in which the second ECG signal is measured. The ECG signal verification apparatus 100 may configure, as a group, the first group and the second group.

The ECG signal verification apparatus 100 also classifies, into a third group, a third ECG signal that is not included in either the first group or the second group. The third group is a group including a third ECG signal having a similarity with a second ECG signal that is less than that of the third ECG signal included in the first group, and a similarity with another third ECG signal that is less than that of the third ECG signal included in the second group. The third ECG signal included in the third group may be an ECG signal measured from another user, or an ECG signal measured in a state that is different from a state in which the ECG signals in the first group and the second group are measured.

In operation 430, the ECG signal verification apparatus 100 sets, to be an additional second ECG signal, a third ECG signal included in a same group as a second ECG signal based on a result of the classifying, and adds the additional second ECG signal to the reference ECG signal set. When the third ECG signals are classified into the first group, the second group, and the third group, the ECG signal verification apparatus 100 sets the third ECG signal included in the first group to be an additional second ECG signal. Also, the ECG signal verification apparatus 100 sets all the third ECG signals included in the first group and the second group to be additional second ECG signals. The ECG signal verification apparatus 100 then adds the newly set, additional second ECG signals to the reference ECG signal set. The ECG signal verification apparatus 100 also removes some of the second ECG signals included in the reference ECG signal set. The removal will be described in greater detail with reference to FIG. 8.

Figure 5:
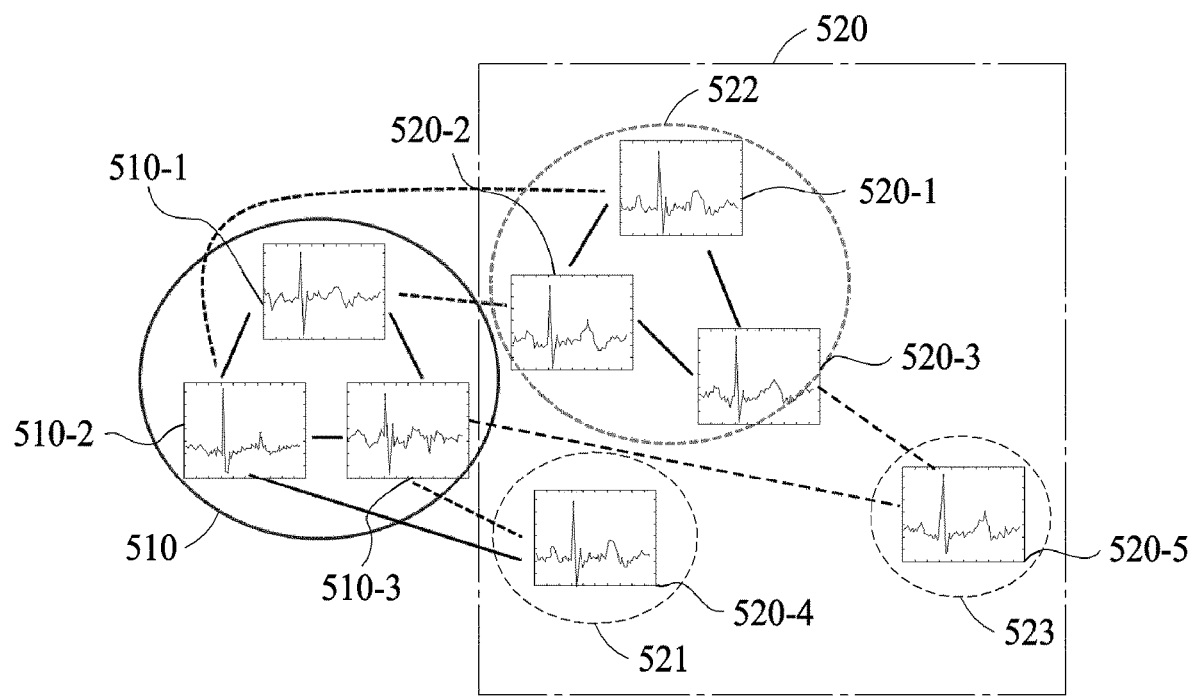
FIG. 5 is a diagram illustrating an example of a method of updating a reference ECG signal set.

FIG. 5 is a diagram illustrating an example of a method of updating a reference ECG signal set.

FIG. 5 illustrates second ECG signals 510-1, 510-2, and 510-3, third ECG signals 520-1, 520-2, 520-3, 520-4, and 520-5, a reference ECG signal set 510, a verified ECG signal set 520, a first group 521, a second group 522, and a third group 523. In the example illustrated in FIG. 5, a connection line between a second ECG signal and a third ECG signal indicates a similarity between the connected ECG signals. A solid line and a broken line used herein indicate a degree of a similarity. A similarity indicated by a connection line illustrated as a solid line may be greater than a similarity indicated by a connection line illustrated as a broken line.

Although eight signals are illustrated in FIG. 5, the number of signals is provided merely as an illustrative example. Thus, the number of signals may be greater than or less than eight. Referring to FIG. 5, the third ECG signal 520-4, among the third ECG signals 520-1 through 520-5 included in the verified ECG signal set 520, is classified into the first group 521. The third ECG signals 520-1, 520-2, and 520-3 are classified into the second group 522. The third ECG signal 520-5 is classified into the third group 523. The ECG signal verification apparatus 100 determines a third ECG signal, among third ECG signals that are classified into groups, to be set to be an additional second ECG signal.

The third ECG signals 520-1, 520-2, and 520-3 have relatively low similarities with the second ECG signals 510-1, 510-2, and 510-3, and relatively high similarities thereamong. The third ECG signals 520-1, 520-2, and 520-3 may have relatively low similarities with other third ECG signals. The third ECG signals 520-1, 520-2, and 520-3 may be measured from a same user, yet measured in a state that is different from a state in which the second ECG signals 510-1, 510-2, and 510-3 are measured from the same user.

The third ECG signal 520-4 has a relatively high similarity with the second ECG signal 510-2, and a relatively low similarity with the second ECG signal 510-3. The third ECG signal 520-4 may be measured in a state that is the same as or similar to a state in which the second ECG signal 510-2 is measured from the same user.

The third ECG signal 520-5 has relatively low similarities with the second ECG signals 510-1, 510-2, and 510-3, and also relatively low similarities with the third ECG signals 520-1, 520-2, 520-3, and 520-4. The third ECG signal 520-5 may be an ECG signal measured from another user, or an ECG signal measured from the same user in a state that is different from states in which the second ECG signals 510-1, 510-2, and 510-3, and the third ECG signals 520-1, 520-2, 520-3, and 520-4 are measured.

The ECG signal verification apparatus 100 sets the third ECG signal 520-4 to be an additional second ECG signal. In addition, the ECG signal verification apparatus 100 removes the third ECG signals 520-1, 520-2, 520-3, and 520-5 from the verified ECG signal set 520. The ECG signal verification apparatus 100 may then verify a first ECG signal using the third ECG signal 520-4 and the second ECG signals 510-1, 510-2, and 510-3. The ECG signal verification apparatus 100 may then set the successfully verified first ECG signal to be a third ECG signal.

Alternatively, the ECG signal verification apparatus 100 sets, to be additional second ECG signals, the third ECG signals 520-1, 520-2, 520-3, and 520-4. In addition, the ECG signal verification apparatus 100 removes the third ECG signal 520-5 from the verified ECG signal set 520. The ECG signal verification apparatus 100 may then verify a first ECG signal using the third ECG signals 520-1, 520-2, 520-3, and 520-4, and the second ECG signals 510-1, 510-2, and 510-3.

The ECG signal verification apparatus 100 may then set the successfully verified first ECG signal to be a third ECG signal.

Figure 6:
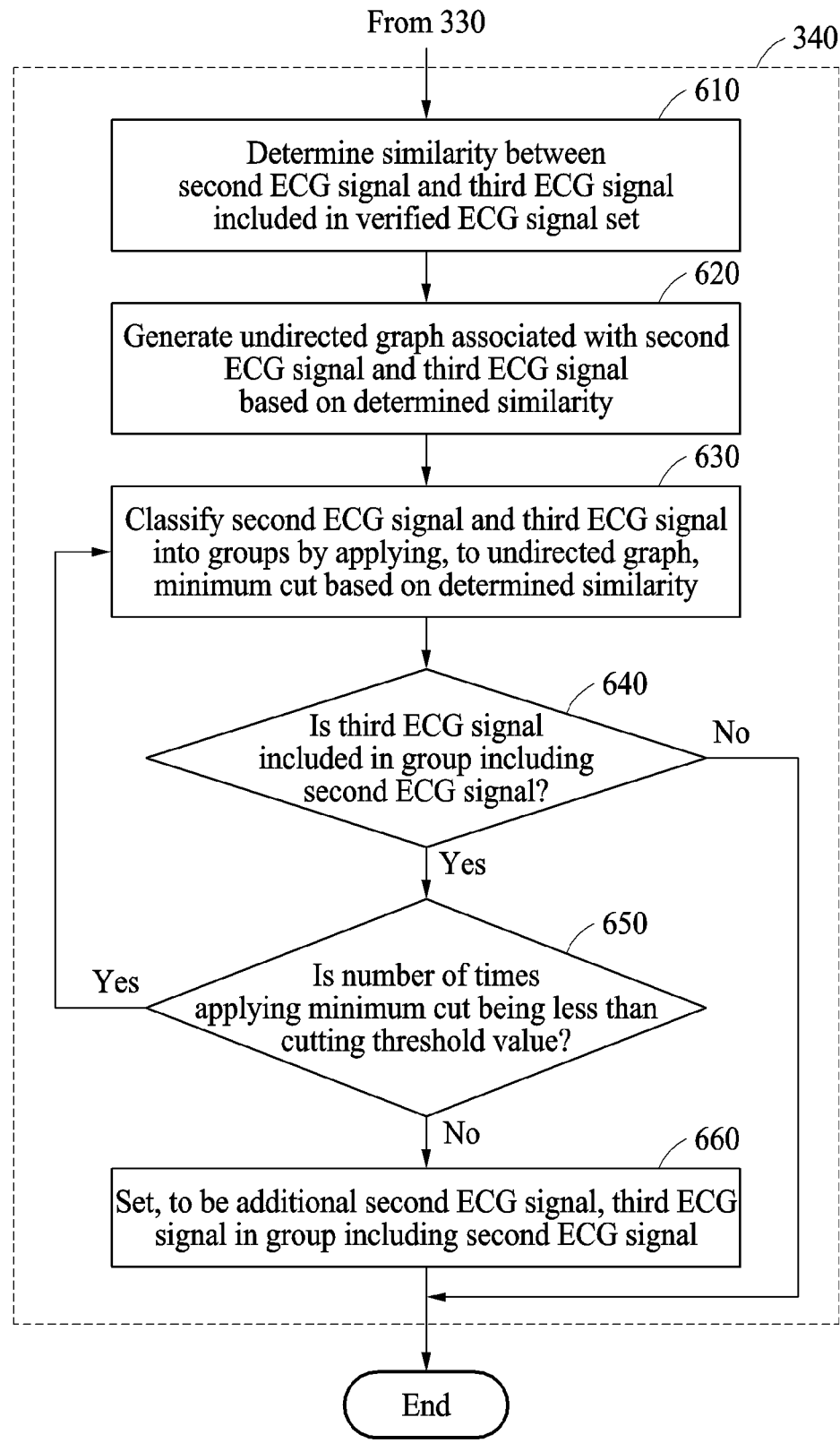
FIG. 6 is a flowchart illustrating another example of a method of updating a reference ECG signal set.

FIG. 6 is a flowchart illustrating another example of a method of updating a reference ECG signal set.

Operation 340 described above with reference to FIG. 3 may include operations 610 through 660 to be described hereinafter with reference to FIG. 6. Referring to FIG. 6, in operation 610, the ECG signal verification apparatus 100 determines a similarity between each of second ECG signals included in a reference ECG signal set and each of third ECG signals included in a verified ECG signal set. The ECG signal verification apparatus 100 may determine the similarity as described in operation 410 of FIG. 4.

In operation 620, the ECG signal verification apparatus 100 generates an undirected graph associated with the second ECG signals and the third ECG signals based on the determined similarity. The undirected graph is a graph that provides information associated with a relationship between the second ECG signals and the third ECG signals. For example, the undirected graph includes each of the second ECG signals and the third ECG signals as a single point, and a connection line connecting two different points. Each connection line may include a similarity between connected two ECG signals as a weight. For example, a weight of a connection line connecting two second ECG signals corresponds to a similarity between the connected two second ECG signals. Similarly, a weight of a connection line connecting a second ECG signal and a third ECG signal corresponds to a similarity between the connected second ECG signal and the connected third ECG signal.

The ECG signal verification apparatus 100 may simplify the undirected graph by removing some of connection lines from the undirected graph. For example, the ECG signal verification apparatus 100 removes a connection line having a similarity that is less than a simplification threshold value. The simplification threshold value used herein is a similarity threshold value of a connection line to be removed to simplify the undirected graph. For example, the simplification threshold value is the same as a verification threshold value. The ECG signal verification apparatus 100 may set, to be relatively high, weights of connection lines connecting the second ECG signals in order not to remove connection lines of the reference ECG signal set. For example, the ECG signal verification apparatus 100 sets the weights of the connection lines that connect the second ECG signals to be a constant value greater than or equal to 1.

In addition, the ECG signal verification apparatus 100 may hold K connection lines having a relatively high similarity among connection lines for a single third ECG signal. The ECG signal verification apparatus 100 may then remove connection lines, excluding the held K connection lines. In this example, K is a preset or specified value, which is an integer greater than 0.

In operation 630, the ECG signal verification apparatus 100 classifies the second ECG signals and the third ECG signals into two groups by applying, to the undirected graph, a minimum cut based on the determined similarity. The minimum cut used herein refers to a cut of connection lines that allows a sum of weights of connection lines to be cut to be minimal. For example, the ECG signal verification apparatus 100 applies the minimum cut to the undirected graph using a Stoer-Wagner algorithm. When the minimum cut is applied, the second ECG signals and the third ECG signals in the undirected graph are classified into the two groups. After the minimum cut is applied, all of the second ECG signals are classified into one group. In this example, ECG signals included in each of the groups may be connected to one another.

When all of the second ECG signals and the third ECG signals in the undirected graph are connected, the ECG signal verification apparatus 100 applies the minimum cut to the entire undirected graph. Conversely, when not all of the second ECG signals and the third ECG signals are connected, the ECG signal verification apparatus 100 applies the minimum cut to a second ECG signal and a third ECG signal that are connected to the second ECG signals. That is, the ECG signal verification apparatus 100 applies the minimum cut to a group including the second ECG signals.

The ECG signal verification apparatus 100 may apply the minimum cut to the undirected graph until the number of times that the minimum cut is applied reaches a cutting threshold value. The cutting threshold value is a preset or specified number of times to apply the minimum cut.

In operation 640, the ECG signal verification apparatus 100 determines whether a third ECG signal is included in the group including a second ECG signal. In response to a determination that the third ECG signal is not included in the group including the second ECG signal, the ECG signal verification apparatus 100 does not update the reference ECG signal set. The ECG signal verification apparatus 100 then removes all of the third ECG signals in the verified ECG signal set.

In response to a determination that the third ECG signal is included in the group including the second ECG signal, the ECG signal verification apparatus 100 performs operation 650. In operation 650, the ECG signal verification apparatus 100 determines whether the number of times that the minimum cut is applied is less than the cutting threshold value. In response to a determination that the number of the times that the minimum cut is applied is less than the cutting threshold value, the ECG signal verification apparatus 100 performs operation 630. The ECG signal verification apparatus 100 then applies the minimum cut to the group including the second ECG signal.

In response to a determination that the number of times that the minimum cut is applied is not less than the cutting threshold, the ECG signal verification apparatus 100 performs operation 660. In operation 660, the ECG signal verification apparatus 100 sets, to be an additional second ECG signal, the third ECG signal included in the group including the second ECG signal. That is, the ECG signal verification apparatus 100 applies, to the undirected graph, the minimum cut a number of times that is equal to the cutting threshold value, and sets the third ECG signal connected to the second ECG signal to be an additional second ECG signal. The ECG signal verification apparatus 100 may obtain an average of third ECG signals included in the group including the second ECG signal, and may set the average to be an additional second ECG signal.

The ECG signal verification apparatus 100 adds the newly set, additional second ECG signal to the reference ECG signal set. In addition, the ECG signal verification apparatus 100 may also remove some of the second ECG signals included in the reference ECG signal set. The removal will be described in greater detail with reference to FIG. 8.

Figure 7:
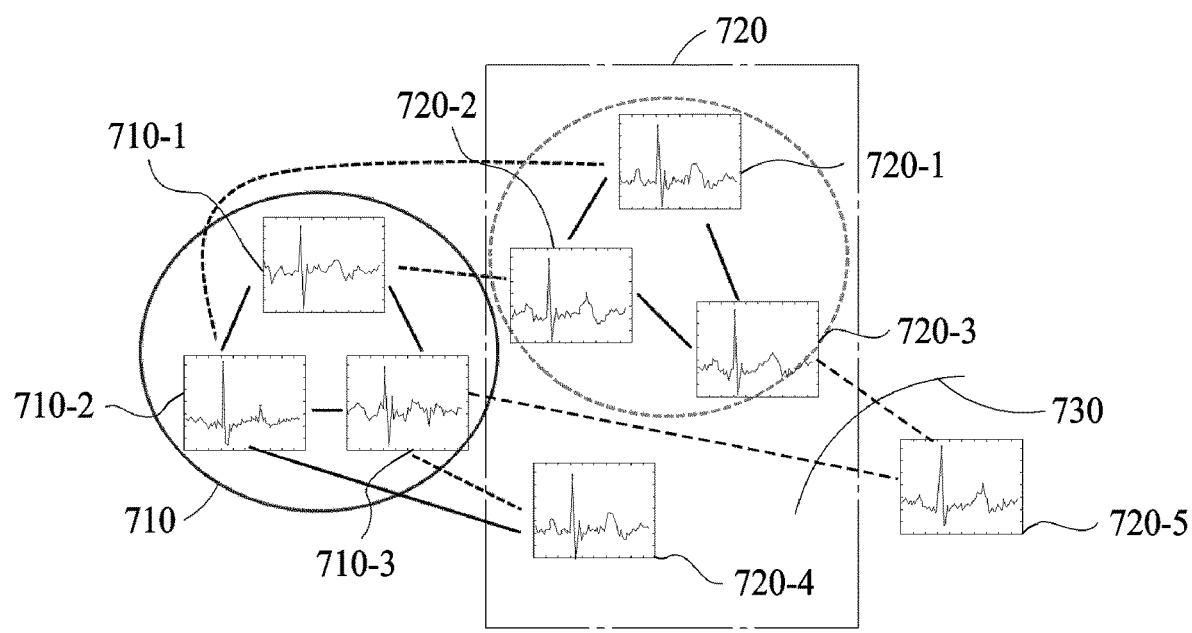
FIG. 7 is a diagram illustrating another example of a method of updating a reference ECG signal set.

FIG. 7 is a diagram illustrating another example of a method of updating a reference ECG signal set.

FIG. 7 illustrates second ECG signals 710-1, 710-2, and 701-3, third ECG signals 720-1, 720-2, 720-3, 720-4, and 720-5, a reference ECG signal set 710, a verified ECG signal set 720, and a final minimum cut 730. FIG. 7 also illustrates connection lines between second ECG signals, third ECG signals, and each of the second ECG signals and each of the third ECG signals. Although eight signals are illustrated in FIG. 7, the number of signals is provided merely as an illustrative example. Thus, the number of signals may be greater than or less than eight. Each of the connection lines includes, as a weight, a similarity between two ECG signals connected by a corresponding connection line. A solid line and a broken line used herein indicate a degree of a similarity. That is, a similarity indicated by a connection line illustrated as a solid line may be greater than a similarity indicated by a connection line illustrated as a broken line.

Referring to FIG. 7, the third ECG signals 720-1, 720-2, and 720-3 have relatively low similarities with the second ECG signals 710-1, 710-2, and 710-3, and relatively high similarities thereamong. The third ECG signals 720-1, 720-2, and 720-3 may be ECG signals measured from a same user, yet measured in a state that is different from a state in which the second ECG signals 710-1, 710-2, and 710-3 are measured from the user.

The third ECG signal 720-4 has a relatively high similarity with the second ECG signal 710-2, and a relatively low similarity with the second ECG signal 710-3. The third ECG signal 720-4 has relatively low similarities with the other third ECG signals 720-1, 720-2, 720-3, and 720-5. The third ECG signal 720-4 may be an ECG signal measured from the user in a state that is the same as or similar to a state in which the second ECG signal 710-2 is measured from the user.

The third ECG signal 720-5 has relatively low similarities with the second ECG signals 710-1, 710-2, and 710-3, and also with the third ECG signals 720-1, 720-2, 720-3, and 720-4. The third ECG signal 720-5 may be an ECG signal measured from another user, or measured in a state that is different from a state in which the second ECG signals 710-1, 710-2, and 710-3, and the third ECG signals 720-1, 720-2, 720-3, and 720-4 are measured.

The final minimum cut 730 is a minimum cut when the number of times that a minimum cut is applied is a cutting threshold value. For example, when the cutting threshold value is five, the final minimum cut 730 is a fifth minimum cut. The second and third ECG signals illustrated in FIG. 7 are classified into two groups based on the final minimum cut 730. The ECG signal verification apparatus 100 then sets the third ECG signals 720-1, 720-2, 720-3, and 720-4 to be additional second ECG signals. The ECG signal verification apparatus 100 adds the newly set, additional second ECG signals to the reference ECG signal set 710. The ECG signal verification apparatus 100 may also remove the third ECG signal 720-5.

The ECG signal verification apparatus 100 may then verify a first ECG signal using the third ECG signals 720-1, 720-2, 720-3, and 720-4, and the second ECG signals 710-1, 710-2, and 710-3. The ECG signal verification apparatus 100 may then set the successfully verified first ECG signal to be a third ECG signal.

Figure 8:
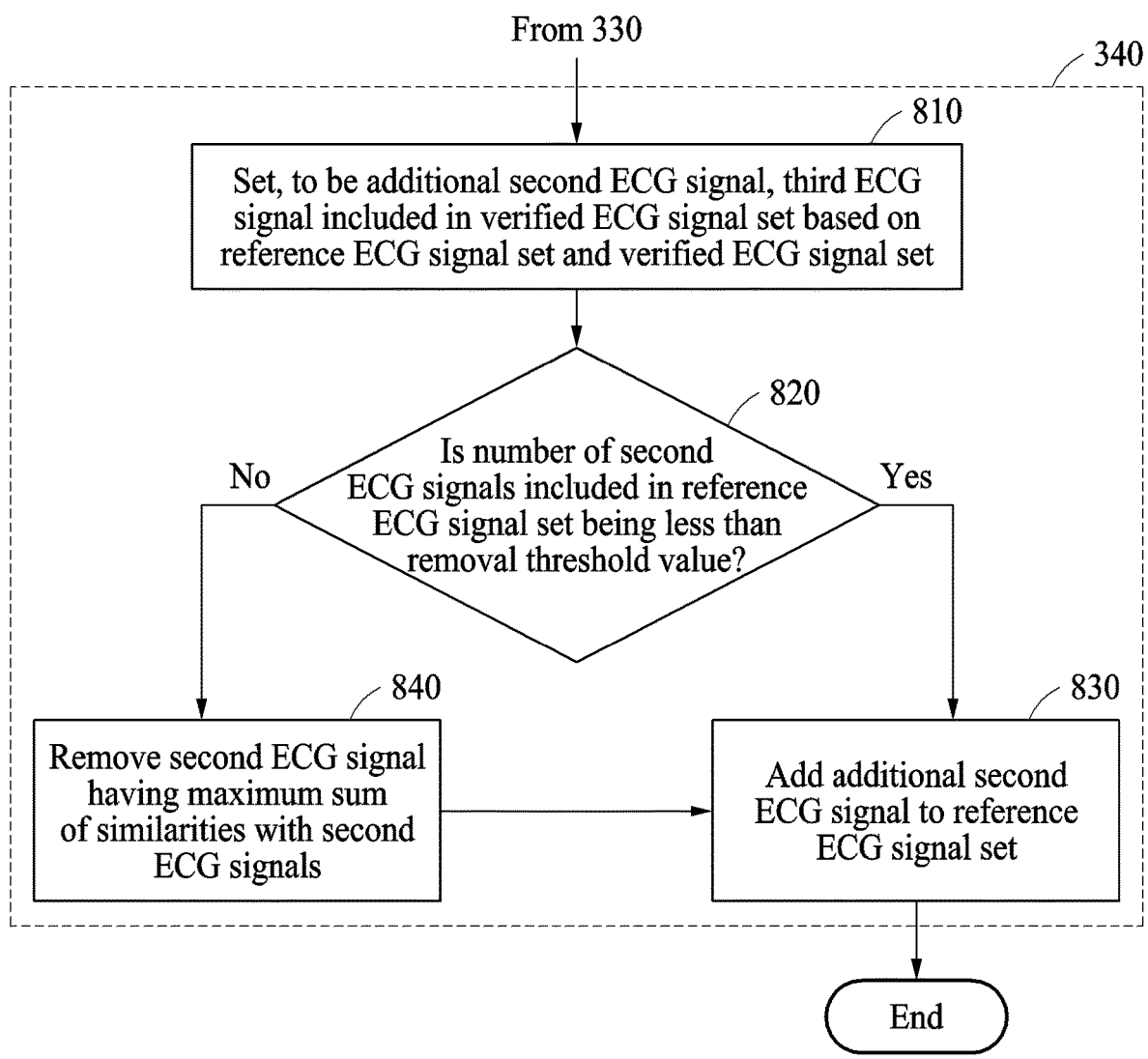
FIG. 8 is a flowchart illustrating a detailed example of a method of updating a reference ECG signal set.

FIG. 8 is a flowchart illustrating a detailed example of a method of updating a reference ECG signal set.

Referring to FIG. 8, in operation 810, the ECG signal verification apparatus 100 sets, to be an additional second ECG signal, a third ECG signal included in a verified ECG signal set based on a reference ECG signal set and the verified ECG signal set. The ECG signal verification apparatus 100 may set the third ECG signal to be the additional second ECG signal through the operations described above with reference to FIG. 4 or 6.

In operation 820, the ECG signal verification apparatus 100 determines whether the number of second ECG signals included in the reference ECG signal set is less than a removal threshold value. The removal threshold value is a maximum number of second ECG signals to be included in the reference ECG signal set. For example, when the removal threshold value is 10, the ECG signal verification apparatus 100 determines whether the number of the second ECG signals included in the reference ECG signal set is less than 10.

In response to a determination that the number of the second ECG signals included in the reference ECG signal set is less than the removal threshold value, the ECG signal verification apparatus 100 performs operation 830. In operation 830, the ECG signal verification apparatus 100 adds the newly set, additional second ECG signal to the reference ECG signal set.

In response to a determination that the number of the second ECG signals included in the reference ECG signal set is not less than the removal threshold value, the ECG signal verification apparatus 100 performs operation 840. In operation 840, the ECG signal verification apparatus 100 removes a second ECG signal having a maximum sum of similarities with other second ECG signals included in the reference ECG signal set among the second ECG signals. For example, the ECG signal verification apparatus 100 determines a sum of similarities of each of the second ECG signals included in the reference ECG signal set with the other second ECG signals included in the reference ECG signal set, and removes the second ECG signal having a maximum sum of similarities. The ECG signal verification apparatus 100 may have second ECG signals corresponding to more various states of a user by reducing a similarity between the second ECG signals in the reference ECG signal set.

Figure 9:
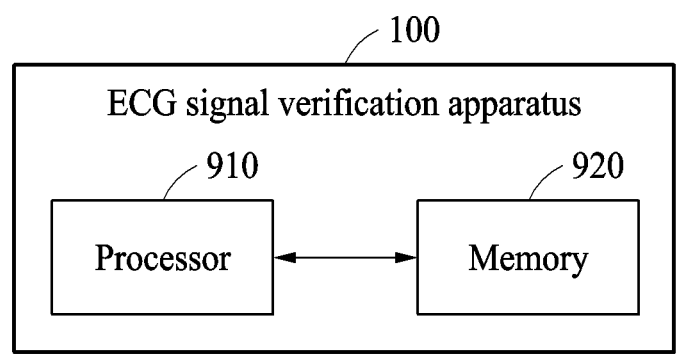
FIG. 9 is a diagram illustrating an example of an ECG signal verification apparatus.

FIG. 9 is a diagram illustrating an example of the ECG signal verification apparatus 100.

Referring to FIG. 9, the ECG signal verification apparatus 100 includes a processor 910 and a memory 920. The memory 920 stores at least one instruction that is implementable by the processor 910. The processor 910 implements the instruction stored in the memory 920. The processor 910 performs at least one operation described above with reference to FIGS. 1 through 9. The processor 910 may update reference verification information to be used for ECG signal verification based on the instruction.

In an example, the processor 910 identifies a first ECG signal measured from a user for ECG signal verification for the user. The processor 910 verifies the first ECG signal using a reference ECG signal set including a second ECG signal to be compared to the first ECG signal. In response to the first ECG signal being successfully verified, the processor 910 sets the successfully verified first ECG signal to be a third ECG signal, and adds the third ECG signal to a verified ECG signal set. The processor 910 then updates the reference ECG signal set by setting the third ECG signal included in the verified ECG signal set to be an additional second ECG signal based on the reference ECG signal set and the verified ECG signal set.

The ECG signal verification apparatus 100, the processor 910, and the memory 920 in FIGS. 1 and 9 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3 to 8 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:
1. A method to update reference verification information used for electrocardiogram (ECG) signal verification, the method comprising:
 identifying a first ECG signal measured from a user for ECG signal verification for the user;

verifying the first ECG signal by comparing a second ECG signal included in a reference ECG signal set with the first ECG signal;
in response to the first ECG signal being successfully verified, setting the successfully verified first ECG signal to be a third ECG signal, and adding the third ECG signal to a verified ECG signal set; and
updating the reference ECG signal set, wherein the updating of the reference ECG signal set comprises setting the third ECG signal added to the verified ECG signal set to be an additional second ECG signal, based on the reference ECG signal set and the verified ECG signal set.

2. The method of claim 1, wherein
the second ECG signal is among second ECG signals included in the reference ECG signal set, and
the verifying of the first ECG signal comprises
determining a verification threshold value based either one or both of a similarity between second ECG signals included in the reference ECG signal set and a quantity of the second ECG signals,
determining a similarity between the first ECG signal and the second ECG signal, and
verifying the first ECG signal by comparing the determined verification threshold value with the determined similarity.

3. The method of claim 1, wherein
the third ECG signal added to the verified ECG signal set is among third ECG signals included in the verified ECG signal set, and
the updating of the reference ECG signal set further comprises
setting the third ECG signal added to the verified ECG signal set to be the additional second ECG signal,
determining that a quantity of the third ECG signals included in the verified ECG signal set is greater than or equal to an update threshold value, and
adding the additional second ECG signal to the reference ECG signal set.

4. The method of claim 1, wherein
the second ECG signal is among second ECG signals included in the reference ECG signal set,
the third ECG signal added to the verified ECG signal set is among third ECG signals included in the verified ECG signal set, and
the updating of the reference ECG signal set further comprises
determining a similarity between each of the second ECG signals included in the reference ECG signal set and each of the third ECG signals included in the verified ECG signal set,
classifying the third ECG signals into groups based on the determined similarity,
setting the third ECG signal added to the verified ECG signal set to be the additional second ECG signal, in response to the third ECG signal added to the verified ECG signal set being included in a group comprising one or more of the second ECG signals based on a result of the classifying, and
adding the additional second ECG signal to the reference ECG signal set.

5. The method of claim 4, wherein the classifying of the third ECG signals into groups comprises
classifying, into a first group, a third ECG signal, among the third ECG signals, having a similarity with a second ECG signal, among the second ECG signals, that is greater than or equal to a first grouping threshold value,
classifying, into a second group, a third ECG signal, among the third ECG signals, having a similarity with a second ECG signal, among the second ECG signals, that is less than the first grouping threshold value and having a similarity with another third ECG signal, among the third ECG signals, that is greater than or equal to a second grouping threshold value, and
classifying, into a third group, a third ECG signal, among the third ECG signals, that is not included in either one of the first group and the second group.

6. The method of claim 5, wherein the adding of the second ECG signal to the reference ECG signal set comprises setting the third ECG signal classified into the first group and the third ECG signal classified into the second group to be additional second ECG signals, and adding the additional second ECG signals to the reference ECG signal set.

7. The method of claim 1, wherein
the second ECG signal is among second ECG signals included in the reference ECG signal set,
the third ECG signal added to the verified ECG signal set is among third ECG signals included in the verified ECG signal set, and
the updating of the reference ECG signal set further comprises
determining a similarity between each of the second ECG signals included in the reference ECG signal set and each of the third ECG signals included in the verified ECG signal set,
generating an undirected graph associated with the second ECG signals and the third ECG signals based on the determined similarity,
classifying the second ECG signals and the third ECG signals into two groups by applying, to the generated undirected graph, a minimum cut based on the determined similarity,
setting the third ECG signal added to the verified ECG signal set to be the additional second ECG signal, in response to the third ECG signal added to the verified ECG signal set being in a group, among the two groups, comprising the second ECG signal, and
adding the additional second ECG signal to the reference ECG signal set.

8. The method of claim 7, wherein the generating of the undirected graph comprises connecting each of the second ECG signals and each of the third ECG signals through a connection line with the determined similarity set as a weight.

9. The method of claim 8, wherein the generating of the undirected graph further comprises simplifying the undirected graph by removing a connection line with a weight less than or equal to a simplification threshold value.

10. The method of claim 1, wherein
the second ECG signal is among second ECG signals included in the reference ECG signal set, and
the updating of the reference ECG signal set further comprises determining a sum of similarities with the second ECG signals for each of the second ECG signals and removing a second ECG signal with a maximum sum of similarities, in response to a quantity of the second ECG signals included in the reference ECG signal set being greater than or equal to a removal threshold value.

11. A non-transitory computer-readable storage medium storing instructions that, when executed by a processor, cause a processor to perform the method of claim 1.

12. An electrocardiogram (ECG) signal verification apparatus to update reference verification information used for ECG signal verification, the ECG signal verification apparatus comprising:
a processor; and
a memory configured to store one or more instructions implementable by the processor,
wherein, in response to the one or more instructions being implemented by the processor, the processor is configured to
identify a first ECG signal measured from a user for ECG signal verification for the user,
verify the first ECG signal using a reference ECG signal set comprising a second ECG signal to be compared with the first ECG signal,
in response to the first ECG signal being successfully verified, set the successfully verified first ECG signal to be a third ECG signal and add the third ECG signal to a verified ECG signal set, and
update the reference ECG signal set by setting the third ECG signal added to the verified ECG signal set to be an additional second ECG signal.

13. The ECG signal verification apparatus of claim 12, wherein
the second ECG signal is among second ECG signals included in the reference ECG signal set, and
the processor is further configured to
determine a verification threshold value based on either one or both of a similarity between second ECG signals included in the reference ECG signal set and a quantity of the second ECG signals,
determine a similarity between the first ECG signal and the second ECG signal included in the reference ECG signal set, and
verify the first ECG signal by comparing the determined verification threshold value with the determined similarity between the first ECG signal and the second ECG signal.

14. The ECG signal verification apparatus of claim 12, wherein
the second ECG signal is among second ECG signals included in the reference ECG signal set,
the third ECG signal added to the verified ECG signal set is among third ECG signals included in the verified ECG signal set, and
the processor is further configured to
determine a similarity between each of second ECG signals included in the reference ECG signal set and each of third ECG signals included in the verified ECG signal set,
classify the third ECG signals into groups based on the determined similarity,
set the third ECG signal added to the verified ECG signal set to be the additional second ECG signal, in response to the third ECG signal added to the verified ECG signal set being included in a group comprising one or more of the second ECG signals based on a result of the classifying, and
add the additional second ECG signal to the reference ECG signal set.

15. The ECG signal verification apparatus of claim 12, wherein the processor is further configured to:
classify, into a first group, a third ECG, among the third ECG signals, signal having a similarity with a second ECG signal, among the second ECG signals, that is greater than or equal to a first grouping threshold value,
classify, into a second group, a third ECG signal, among the third ECG signals, having a similarity with a second ECG signal, among the second ECG signals, that is less than the first grouping threshold value and having a similarity with another third ECG signal, among the third ECG signals, that is greater than or equal to a second grouping threshold value, and
classify, into a third group, a third ECG, among the third ECG signals, that is not included in either one of the first group and the second group.

16. The ECG signal verification apparatus of claim 15, wherein the processor is further configured to set the third ECG signal included in the first group and the third ECG signal included in the second group to be additional second ECG signals, and add the additional second ECG signals to the reference ECG signal set.

17. The ECG signal verification apparatus of claim 12, wherein
the second ECG signal is among second ECG signals included in the reference ECG signal set,
the third ECG signal added to the verified ECG signal set is among third ECG signals included in the verified ECG signal set, and
the processor is further configured to
determine a similarity between each of the second ECG signals included in the reference ECG signal set and each of the third ECG signals included in the verified ECG signal set,
generate an undirected graph associated with the second ECG signals and the third ECG signals based on the determined similarity,
classify, into two groups, the second ECG signals and the third ECG signals by applying, to the generated undirected graph, a minimum cut based on the determined similarity,
set the third ECG signal added to the verified ECG signal set to be the additional second ECG signal, in response to the third ECG signal added to the verified ECG signal set being in a group, among the two groups, comprising the second ECG, and
add the additional second ECG signal to the reference ECG signal set.

18. The ECG signal verification apparatus of claim 17, wherein the processor is further configured to connect each of the second ECG signals and each of the third ECG signals through a connection line with the determined similarity set as a weight.

19. The ECG signal verification apparatus of claim 18, wherein the processor is further configured to simplify the undirected graph by removing a connection line with a weight less than or equal to a simplification threshold value.

20. The ECG signal verification apparatus of claim 12, wherein
the second ECG signal is among second ECG signals included in the reference ECG signal set, and
the processor is further configured to
determine a sum of similarities with the second ECG signals for each of the second ECG signals and remove a second ECG signal, among the second ECG signals, with a maximum sum of similarities, in response to a quantity of the second ECG signals included in the reference ECG signal set being greater than or equal to a removal threshold value.

* * * * *